United States Patent
Flachman et al.

(10) Patent No.: US 6,348,039 B1
(45) Date of Patent: Feb. 19, 2002

(54) RECTAL TEMPERATURE SENSING PROBE

(75) Inventors: Jonathan L. Flachman, Robbinsdale; James V. Kauphusman, Champlin; Jonathan R. McGrath, Chanhassen; Gregg S. Sutton, Maple Grove, all of MN (US)

(73) Assignee: Urologix, Inc., Minneapolis, MN (US)

( * ) Notice: Subject to any disclaimer, the term of this patent is extended or adjusted under 35 U.S.C. 154(b) by 0 days.

(21) Appl. No.: 09/545,696

(22) Filed: Apr. 7, 2000

Related U.S. Application Data

(60) Provisional application No. 60/128,636, filed on Apr. 9, 1999.

(51) Int. Cl.⁷ ................................................. A61B 5/00
(52) U.S. Cl. ....................................... 600/549; 600/486
(58) Field of Search ................................ 600/549, 587, 600/486

(56) References Cited

U.S. PATENT DOCUMENTS

| | | | |
|---|---|---|---|
| 4,046,139 A | 9/1977 | Horn | 128/2 H |
| 4,311,154 A | 1/1982 | Sterzer et al. | 128/804 |
| 4,662,383 A | 5/1987 | Sogawa et al. | 128/784 |
| 4,676,258 A | 6/1987 | Inokuchi et al. | 128/804 |
| 4,813,429 A | 3/1989 | Eshel et al. | 128/736 |
| 4,924,863 A | 5/1990 | Sterzer | 606/27 |

(List continued on next page.)

FOREIGN PATENT DOCUMENTS

| | | |
|---|---|---|
| EP | 0 105 677 | 9/1983 |
| EP | 0 248 758 | 5/1987 |
| EP | 0 253 677 | 7/1987 |
| EP | 0 370 890 | 11/1989 |
| EP | 0 519 958 | 3/1991 |
| EP | 0 485 323 | 11/1991 |
| EP | 0 646 359 | 10/1994 |
| JP | 63-177867 | 7/1988 |
| WO | WO 93/02748 | 7/1992 |
| WO | WO 94/26178 | 5/1994 |

OTHER PUBLICATIONS

"Transurethral Microwave Thermotherapy for Benign Prostatic Hypertrophy" by Blute, *Mediguide to Urology*, vol. 4, Issue 6, pp. 1–8, 1991.

"Microwave Applicators for Localized Hyperthermia Treatment of Malignant Tumors" by Mendecki et al., *Journal of Bioengineering*, vol. 1, pp. 511–518, 1977.

(List continued on next page.)

*Primary Examiner*—John P. Lacyk
*Assistant Examiner*—Pamela Wingood
(74) *Attorney, Agent, or Firm*—Kinney & Lange, P.A.

(57) ABSTRACT

A rectal thermosensing unit includes, according to one aspect thereof, an elongate member having an inflation lumen extending therethrough. An inflatable balloon is supported by the elongate member. An interior of the inflatable balloon is in fluid communication with the inflation lumen. An insertion lumen extends through the elongate member. An introducer is insertable into the insertion lumen. At least one temperature sensing device is supported by the inflatable balloon. The rectal thermosensing probe is located in a rectum by inserting the introducer into the inflation lumen, inserting the inflatable balloon supported by the elongate member having the introducer inserted in the insertion lumen therein into the rectum, removing the introducer from the insertion lumen, and inflating the inflatable balloon by providing fluid through the inflation lumen. According to another aspect of the rectal thermosensing unit, a body of the unit is passively expandable to support the temperature sensing device against the rectum. The passively expandable body is compressed, inserted into the rectum while compressed, and allowed to passively expand to conform to the shape of the rectal cavity. A ventilation tube is provided through the body of the unit to allow for gas to escape from the rectum.

17 Claims, 9 Drawing Sheets

U.S. PATENT DOCUMENTS

| | | | |
|---|---|---|---|
| 4,950,267 A | | 8/1990 | Ishihara et al. ............... 606/12 |
| 4,967,765 A | | 11/1990 | Turner et al. ............... 128/785 |
| 5,106,360 A | | 4/1992 | Ishiwara et al. ............... 600/2 |
| 5,234,004 A | | 8/1993 | Hascoet et al. ............. 607/116 |
| 5,335,669 A | * | 8/1994 | Tibon et al. ................ 600/549 |
| 5,391,197 A | | 2/1995 | Burdette et al. .............. 607/97 |
| 5,404,881 A | | 4/1995 | Cathaud et al. .......... 128/653.1 |
| 5,415,654 A | | 5/1995 | Daikuzono ................... 606/15 |
| 5,474,071 A | | 12/1995 | Chapelon et al. ...... 128/660.03 |
| 5,484,400 A | | 1/1996 | Edwards et al. .............. 604/22 |
| 5,487,740 A | | 1/1996 | Sulek et al. .................. 606/15 |
| 6,142,993 A | * | 11/2000 | Whayne et al. ............... 606/41 |

OTHER PUBLICATIONS

"Thermometry Considerations in Localized Hyperthermia", by Cetas et al., *Med. Phys.* 5(2), Mar./Apr. 1978, pp. 79–91.

"Radiofrequency–Induced Hyperthermia in the Prostate", by J. Scheiblich et al., *Journal of Microwave Power*, 1982, pp. 472–478.

"Microwave Applicator for Transurethral Hyperthermia of Benign Prostatic Hyperplasia", by Astrahan et al., *Int. J. Hyperthermia*, 1989, vol. 5, No. 3, 283–296.

"Single–Session Transurethral Microwave Thermotherapy for the Treatment of Benign Prostatic Obstruction", by Carter et al., *Journal of Endourology*, vol. 5, No. 2, 1991, pp. 137–144.

"Interstitial Temperature Measurements During Transurethral Microwave Hyperthermia" by Astrahan et al., *The Journal of Urology*, vol. 145, pp. 304–308, Feb. 1991.

* cited by examiner

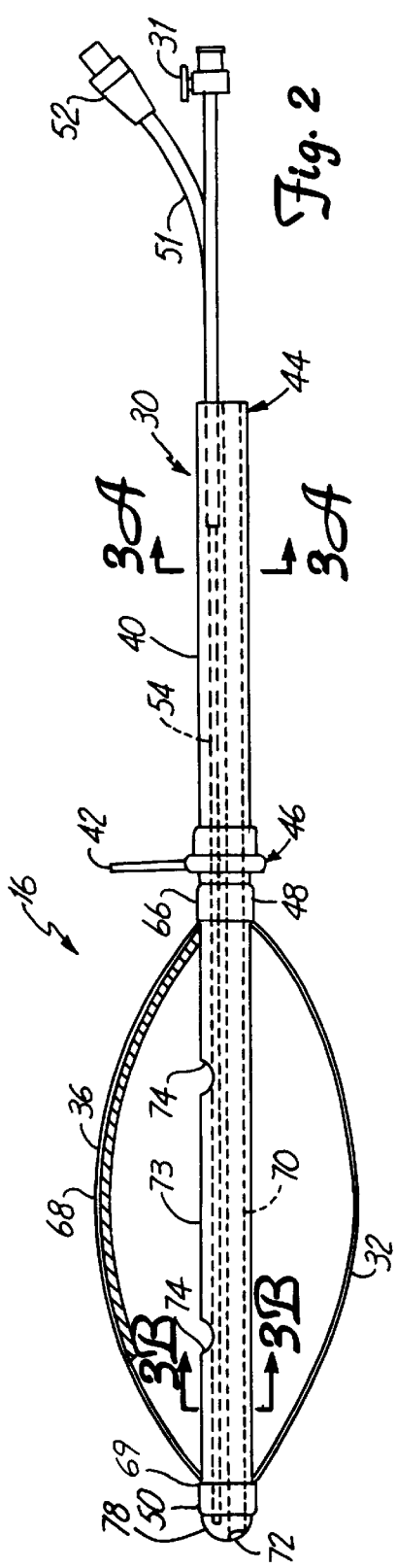
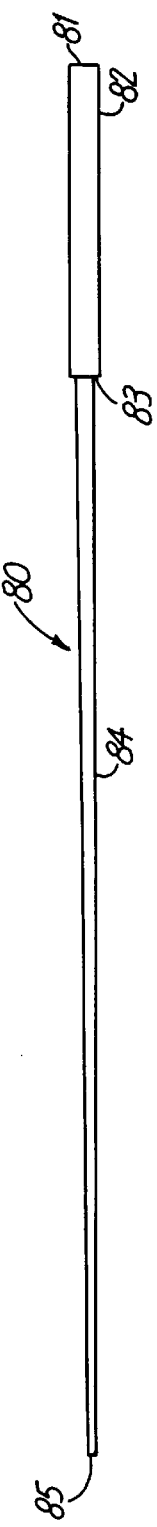

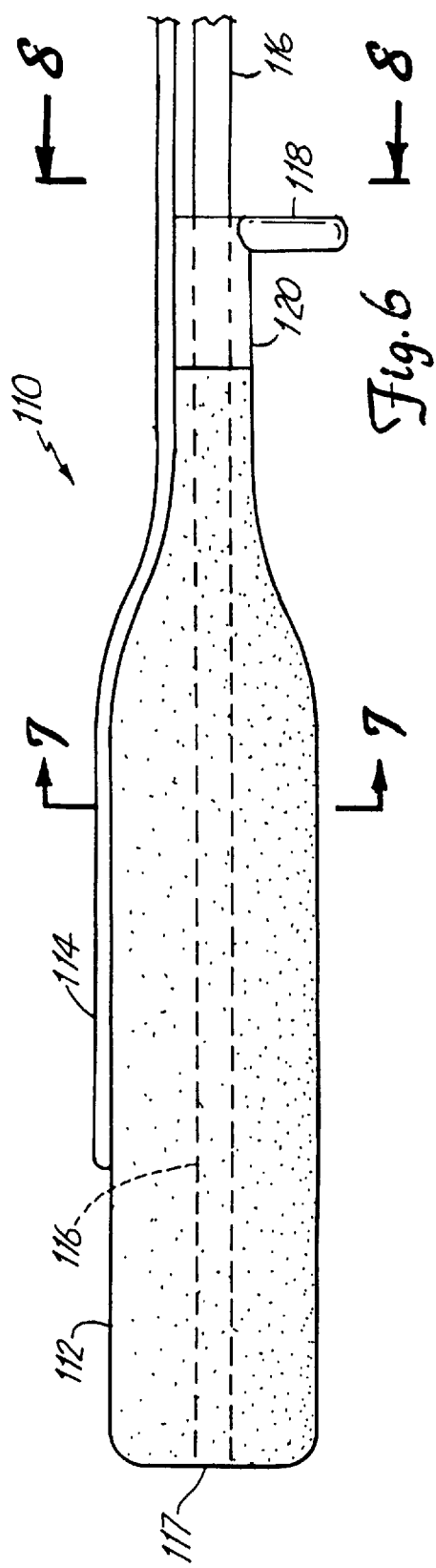
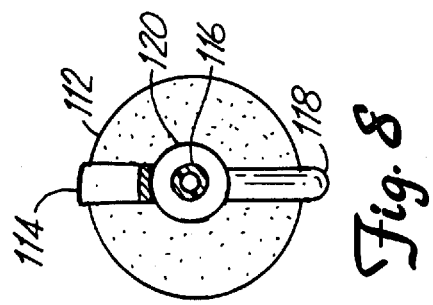
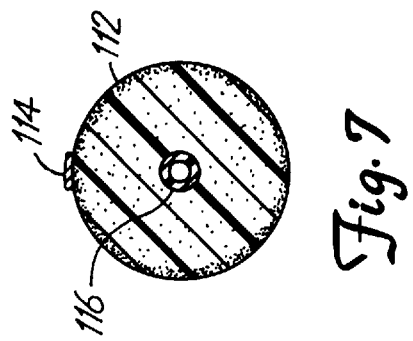

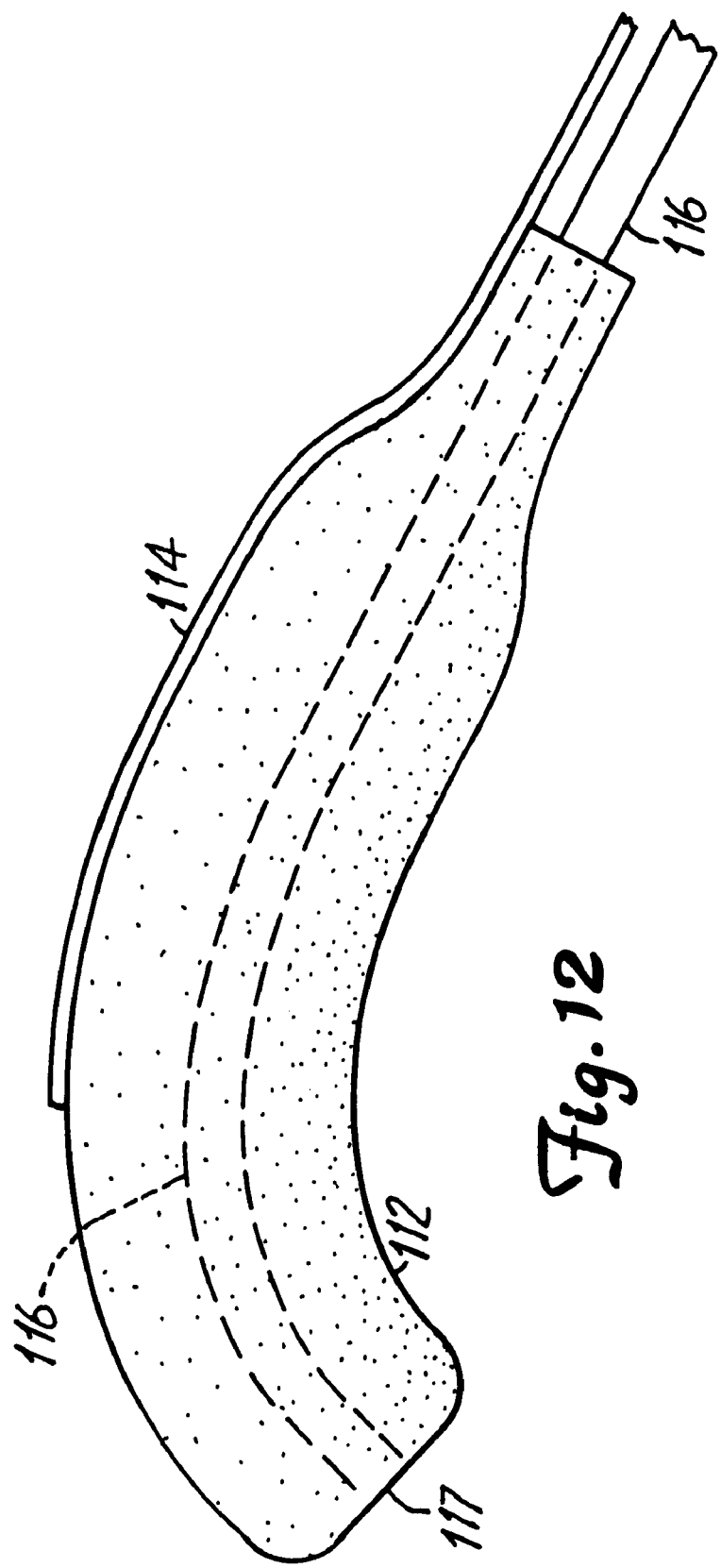

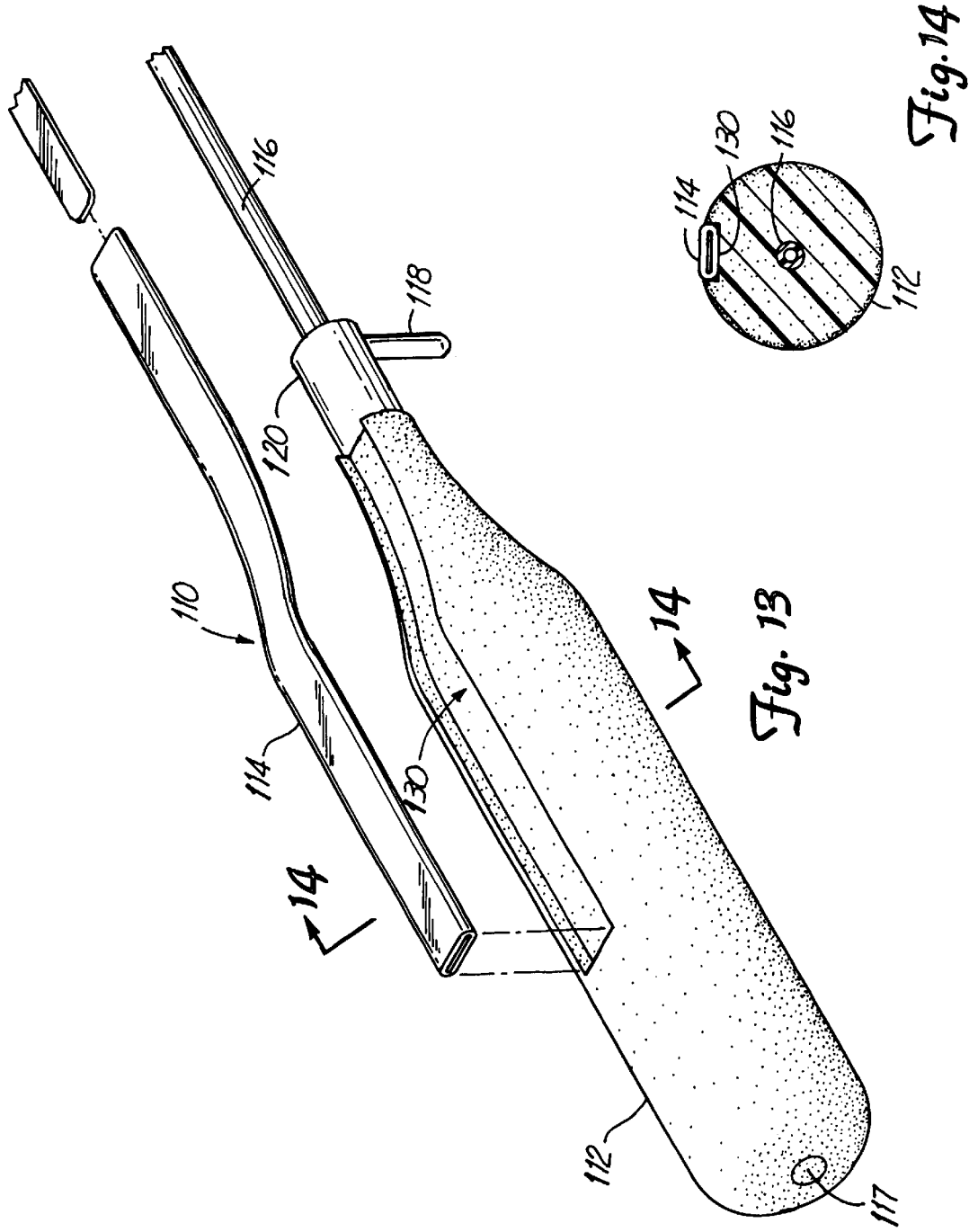

RECTAL TEMPERATURE SENSING PROBE

CROSS-REFERENCE TO RELATED APPLICATION(S)

This application claims the benefit of U.S. Provisional Application No. 60/128,636 filed Apr. 9, 1999 for "Rectal Temperature Sensing Probe" by J. Flachman, J. McGrath, W. Sutton, G. Sutton, J. Kauphusman and M. J. Tolkoff.

BACKGROUND OF THE INVENTION

The present invention relates to a thermnosensing probe for sensing rectal temperature of a patient. In particular, the present invention relates to rectal probe designs taking the form of a balloon thermosensing probe that includes an insertion lumen for allowing gas to escape from the rectum and for receiving an introducer to facilitate insertion of the balloon into the rectum, and alternatively or in combination a thermosensing device having a body made of open-cell foam which is capable of conforming to the shape of a rectal cavity into which it is inserted.

The prostate gland is a complex, chestnut-shaped organ which encircles the urethra immediately below the bladder and lies immediately adjacent the rectum. This relatively small organ, which is the most frequently diseased of all internal organs, is the site of a common affliction among older men, benign prostatic hyperplasia (BPH), as well as a more serious affliction, cancer. BPH is a non-malignant, bilateral nodular tumorous expansion of prostate tissue occurring mainly in the transition zone of the prostate. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

A fairly recent treatment method for BPH involves microwave thermal therapy, in which microwave energy is employed to elevate the temperature of tissue surrounding the prostatic urethra above about 45° C., thereby thermally damaging the tumorous BPH tissue. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation and generates a radiation pattern which encompasses and necroses the tumorous prostatic tissue. The necrosed intraprostatic tissue is subsequently reabsorbed by the body, thereby relieving an individual from the symptoms of BPH.

One type of thermal therapy treatment of BPH is transurethral microwave thermal therapy. This method of treatment positions a Foley-type catheter containing a microwave antenna within the urethra adjacent to the prostate gland. The microwave antenna is energized to heat and necrose a selected volume of tumorous prostatic tissue up to 2.0 centimeters from the urethra, by raising the temperature of the selected tissue to a temperature above about 45° C. for a time sufficient to necrose the tissue.

Due to the relatively close proximity of the rectum to the urethra, it is critically important in the course of transurethral thermal therapy that the temperature of the rectum is maintained below a threshold temperature. Rectal temperatures greater than the threshold may cause significant damage to the rectum.

Typically, the temperature of rectal tissue adjacent the prostate is measured and monitored with a rectal temperature sensing probe. The probe supports one or more temperature sensing elements against a wall of the rectum adjacent to the prostate to provide the physician with essential information for controlling the location and degree of heat induced in the prostate. In providing a rectal probe to measure the temperature of rectal tissue adjacent the prostate, it is desirable to maintain the position of a temperature sensing device supported by the probe directly adjacent to the rectal wall to provide optimally accurate temperature readings. Rectal tissue should not be compressed by the temperature sensing probe, since compression tends to reduce blood flow and increase the susceptibility of the rectal tissue to thermal damage. Compression of rectal tissue also compresses the prostate, which reduces the distance between the urethra and the rectal wall and thereby increases rectal temperatures due to heat energy delivered from the urethra. The rectal probe should be easily insertable without deforming or causing trauma to rectal tissue, and should include means for ventilating gas built up in the rectum while the probe is inserted.

Many devices used to monitor the temperature of the rectal wall during thermal therapy involve the use of a balloon for anchoring temperature sensing devices in the rectal cavity. To operate these devices, a balloon is first inserted into the rectum, and is then inflated to engage the wall of the rectum and hold the temperature sensing devices in place. Proper use of this device requires human manipulation and care, introducing the risk of human error. For example, over-inflation of the balloon could potentially compress rectal tissue and thereby lead to overheating of rectal tissue as mentioned previously, or the balloon could break or inadvertently deflate. While balloon devices are effective for their purpose when properly utilized, an alternate design could potentially represent an improvement over the state of the art.

SUMMARY OF THE INVENTION

The present invention is a rectal thermosensing unit for sensing temperature of rectal tissue. The unit includes an elongate member having an inflation lumen extending therethrough. An inflatable balloon is supported by the elongate member. An interior of the inflatable balloon is in fluid communication with the inflation lumen. An insertion lumen extends through the elongate member, and an introducer is insertable into the insertion lumen. At least one temperature sensing device is supported by the inflatable balloon.

Another aspect of the present invention is a method of locating in a rectum a rectal thermosensing probe having an elongate member supporting an inflatable balloon, which in turn supports a temperature sensing device. An inflation lumen and an insertion lumen are provided, extending through the elongate member. An introducer is inserted into the insertion lumen. The inflatable balloon supported by the elongate member is inserted into the rectum. The introducer is removed from the insertion lumen, and the inflatable balloon is inflated by providing fluid through the inflation lumen.

Another form of the present invention is a rectal thermosensing unit having a passively expandable body with first and second ends. An elongate member supports the body between the first and second ends. A temperature sensing device is supported by the body, and a handle is attached to the elongate member at the second end of the body. In one embodiment, a sheath is deployable around the body to compress the body to a preselected diameter for insertion into a rectum.

The present invention also encompasses a method of sensing temperature of rectal tissue. A passively expandable body having an uncompressed outer diameter approximating a rectal cavity is compressed. The body carries at least one temperature sensor. The compressed body is inserted into the rectal cavity. The body is then allowed to passively expand to conform to a shape of the rectal cavity.

A still further aspect of the invention is a method of forming a rectal thermosensing unit. A passively expandable body is formed having an uncompressed outer diameter approximating a rectal cavity. A passageway is formed through the body, and an elongate member is bonded to the body in the passageway. A temperature sensing device is attached to the body, and a handle is either attached to or formed from the elongate member.

BRIEF DESCRIPTION OF THE DRAWINGS

FIG. 2 is a side elevational view of the rectal thermosensing unit of a first embodiment of the present invention.

FIG. 3A is a cross-sectional view of the rectal thermosensing unit taken along lines 3A—3A of FIG. 2.

FIG. 3B is a cross-sectional view of the rectal thermosensing unit taken along lines 3B—3B of FIG. 2.

FIG. 4 is a side elevational view of an introducer for facilitating insertion of the rectal thermosensing unit shown in FIG. 2.

FIG. 6 is a side view of a rectal thermosensing device according to a second embodiment of the present invention.

FIG. 7 is a sectional view taken along line 7—7 in FIG. 6.

FIG. 8 is a sectional view taken along line 8—8 in FIG. 6.

FIG. 12 is a diagram illustrating a rectal thermosensing device according to an alternate version of the second embodiment of the present invention.

FIG. 13 is an exploded perspective view of a rectal thermosensing device according to a further alternate version of the second embodiment of the present invention.

FIG. 14 is a sectional view taken along line 14—14 in FIG. 13.

DETAILED DESCRIPTION OF THE PREFERRED EMBODIMENTS

A. Rectal Thermosensing Probe with Introducer

Figure 1:
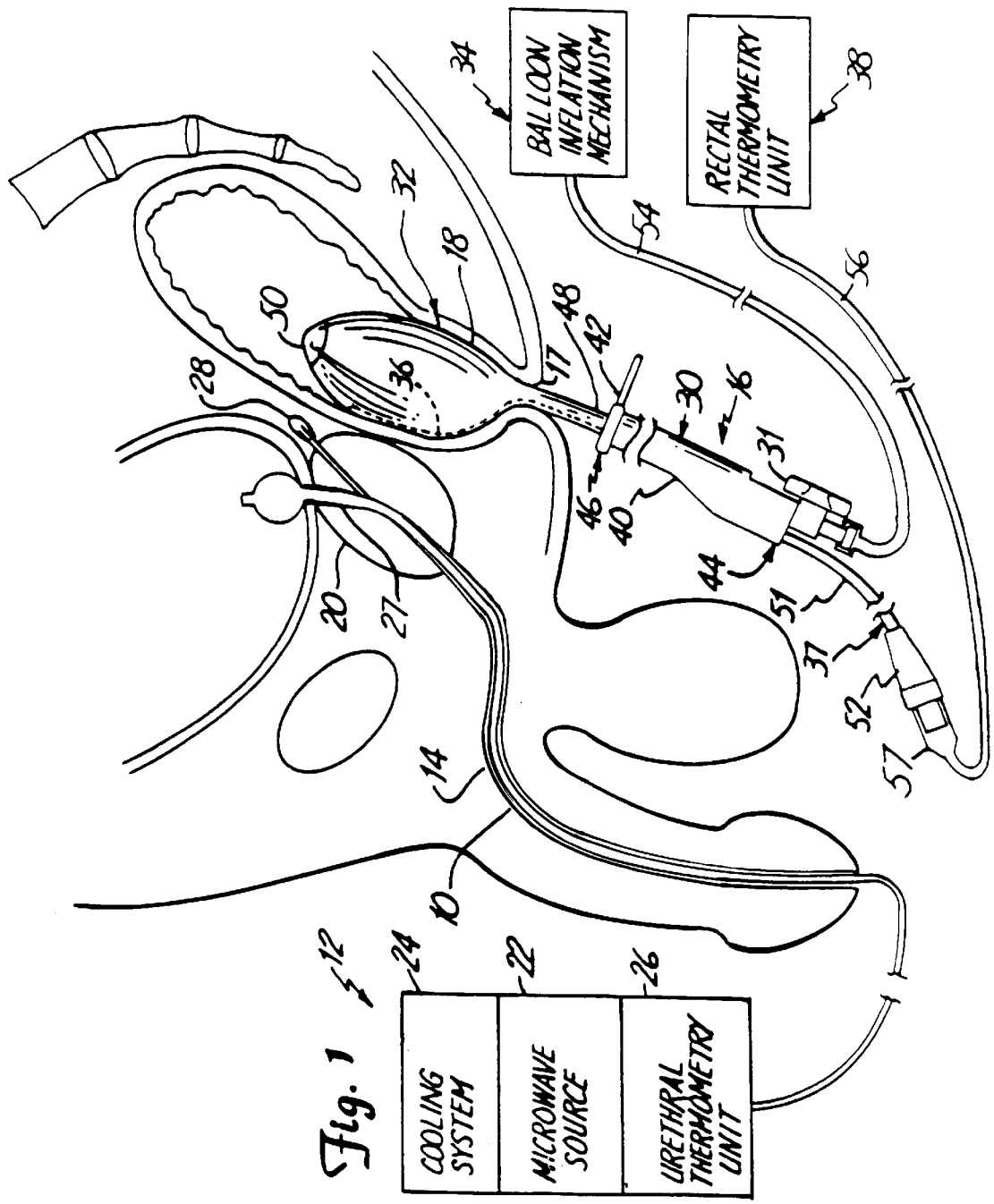
FIG. 1 is a vertical sectional view of a male pelvic region illustrating a transurethral thermal therapy device positioned in the urethra and a rectal thermosensing unit positioned within the rectum of the male pelvic region.

FIG. 1 is a vertical sectional view of a male pelvic region illustrating catheter 10 of transurethral thermal therapy system 12 properly positioned within urethra 14 and rectal thermosensing unit 16 properly positioned within rectum 18. Transurethral thermal therapy system 12 heats benign tumorous tissue growth within prostate 20 surrounding urethra 14 to necrose the tumorous tissue. Catheter 10 of transurethral thermal therapy system 12 preferably comprises a microwave antenna-containing catheter including a multi-lumen shaft. Transurethral thermal therapy system 12 further includes a microwave source 22, a cooling system 24 and a urethral thermometry unit 26. As described in further detail in U.S. Pat. No. 5,413,588 entitled DEVICE FOR ASYMMETRICAL THERMAL THERAPY WITH HELICAL DIPOLE MICROWAVE ANTENNA, which is hereby incorporated by reference, transurethral thermal therapy system 12 treats benign tumorous tissue growth within prostate 20 with a microwave generating source 22, which energizes an antenna 27 located within catheter 10 and positioned within urethra 14 across prostate 20. Energization of antenna 27 causes antenna 27 to emit electromagnetic energy which heats tissue within prostate 20. To avoid unnecessary and undesirous damage to urethra 10 and adjacent healthy tissues, cooling system 24 supplies a cooling fluid through the multi-lumen shaft of catheter 10 to precisely control temperature distribution of tissue surrounding catheter 10 based upon temperatures of the tissues sensed by urethral thermometry unit 26.

To further measure and monitor the temperature of tissue adjacent prostate 20 so as to prevent unnecessary damage to rectum 18 and otherwise healthy tissue surrounding prostate 20, rectal thermosensing unit 16 is positioned within rectum 18 adjacent prostate 20. Rectal thermosensing unit 16 generally includes handle 30, control valve 31, balloon 32, balloon inflation mechanism 34, at least one temperature sensing device 36, sensing device connector assembly 37 and rectal thermometry unit 38. Handle 30 is a generally elongate member having a central body 40 and a flag 42. Central body 40 includes a first end 44 and a second end 46. First end 44 of central body 40 is located adjacent control valve 31 and connector assembly 37. Second end 46 of handle 30 is coupled to balloon 32 and temperature sensing device 36. Central body 40 preferably has a length extending between first end 44 and second end 46 sufficient to allow a physician to easily grasp handle 30. Handle 30 preferably has a length of about 6.5 inches and a diameter of about 0.5 inches. Handle 30 enables a physician to easily manipulate balloon 32 and temperature sensing device 36 for properly positioning temperature sensing device 36 within rectum 18 adjacent prostate 20.

Flag 42 generally comprises an elongate protrusion radially extending outward from central body 40 at a selected angle or position relative to balloon 32 and temperature sensing device 36. Flag 42 is located at the second end 46 of handle 30 and indicates the orientation of balloon 18 and temperature sensing device 36 within rectum 18. Flag 42 further indicates when balloon 32 and temperature sensing device 36 have been fully inserted into rectum 18. As can be appreciated, a variety of indicating mechanisms such as indexing marks, grooves or alternative projections may be used in lieu of flag 42 for permitting a physician to visually determine the orientation and location of balloon 32 and temperature sensing device 36 within rectum 18.

Control valve 31 preferably comprises a standard stop cock or one-way valve for regulating inflation of balloon 32 by balloon inflation mechanism 34. Control valve 31 is attached to handle 30 and is fluidly coupled to an inflation lumen 54 (shown in FIGS. 2 and 3) extending through handle 30. Control valve 31 regulates the flow of inflation fluid from balloon inflation mechanism 34 through inflation lumen 54 into balloon 32. Because control valve 31 is positioned adjacent handle 30, a physician may easily manipulate balloon 32 while also adjusting the rate of inflation of balloon 32.

Balloon 32, upon inflation, is a generally oval-shaped balloon having a first end 48 and a second end 50. First end 48 of balloon 32 is coupled to second end 46 of handle 30. In a preferred embodiment, balloon 32 is manufactured from a flexible, elastic material such as 50 durometer silicone or urethane. The rectal probe consisting of balloon 32 and its associated temperature sensing device 36 has a relatively low overall weight and is able to maintain its positioning within the rectum when inflated. Because balloon 32 is oval-shaped, balloon 32 has an extremely large surface area which may be positioned in contact with the rectal tissue upon inflation. Consequently, balloon 32, upon inflation, sufficiently engages the wall of the rectum to maintain balloon 32 and temperature sensing device 36 within the rectum during treatment without severely compressing rectal tissue. By avoiding compression of rectal tissue and the blood vessels therein, the risk of thermal damage to rectal tissue is substantially reduced.

Prior to a transurethral thermal therapy treatment, balloon 32 is inserted into rectum 18 in an uninflated state. Once inserted into rectum 18, balloon 32 is inflated by balloon inflation mechanism 34. Balloon inflation mechanism 34 preferably inflates balloon 32 with a gas such as air to a selected inflation volume and pressure so as to cause balloon 32 to assume its oval shape as closely as possible and to engage the rectal wall without compressing adjacent tissue. Because balloon 32 is preferably inflated with a gas such as air, rather than a liquid, the temperature effects of the inflation medium upon the temperature sensing device 36 are minimized, resulting in more accurate temperature measurements. In addition, because balloon 32 is preferably inflated with a gas, rather than a liquid, balloon 32 is lighter in weight and better maintains its positioning within the rectum. Upon being inflated by balloon inflation mechanism 34, balloon 32 positions and maintains temperature sensing device 36 in contact with tissue of rectum 18 adjacent prostate 20.

Balloon inflation mechanism 34 is conventionally known and includes an inflation lumen 54 which is in fluid communication with an interior of balloon 32. Balloon inflation mechanism 34 supplies pressurized fluid through inflation lumen 54 into the interior of balloon 32 to inflate balloon 32 to a desired size and pressure.

Temperature sensing device 36 preferably comprises an elongate strip of a plurality of temperature sensors which are supported along an exterior surface of balloon 32. Temperature sensing device 36 extends between first end 48 and second end 50 of balloon 32 and senses temperature of tissue of rectum 18 proximate prostate 20. Temperature sensing device 36 is electrically connected to rectal thermometry unit 38 by sensing device connector assembly 37 so as to transmit signals correlating to sensed temperatures to rectal thermometry unit 38.

Sensing device connector assembly 37 connects temperature sensing device 36 and rectal thermometry unit 38 and includes cable 51 and connector 52. Cable 51 preferably extends through central body 40 of handle 30 and has a first end connected to temperature sensing device 36 and a second end electrically connected to connector 52. Connector 52 preferably comprises a standard eight pin connector configured for mating with a corresponding connector of rectal thermometry unit 38.

Rectal thermometry unit 38 is conventionally known and includes cable 56 and connector 57. Connector 57 mates with connector 52 to electrically connect temperature sensing device 36 to rectal thermometry unit 38 for the transmission of electrical signals corresponding to sensed temperature values. Rectal thermometry unit 38 receives signals from temperature sensing device 36 and converts the signals into temperature values of the tissue of rectum 18. In one preferred embodiment, the temperature values are displayed and/or transmitted to transurethral thermal therapy system 12 for closed loop temperature control of system 12.

FIGS. 2–4 illustrate handle 30, balloon 32 and temperature sensing device 36 in greater detail. FIG. 2 is a side elevational view of thermosensing unit 16 with the interiors of handle 30, balloon 32 and balloon supporting member 73 shown in dashed lines to illustrate the relationship between handle 30, balloon 32 and balloon supporting member 73. Balloon supporting member 73 may be composed of a material such as urethane or silicone, for example, and may be attached to handle 30 by adhesive or thermal bonding, for example, to form a two-piece elongate member along the length of the unit. In another embodiment, balloon supporting member 73 is an extension of handle 30 as a single elongate member spanning the unit. Central body 40 of handle 30 includes isolated lumens defining sensor cable lumen 62, balloon inflation lumen 54 and insertion lumen 70, as illustrated in FIG. 3A. Balloon inflation lumen 54 extends through body 40 of handle 30 from first end 44 to second end 46 of handle 30, and also extends through the interior of balloon 32 within balloon supporting member 73 to tip 78. Inflation openings 74 are provided in balloon supporting member 73 so that inflation lumen 54 is in fluid communication with the interior of balloon 32. Inflation lumen 54 is in fluid communication with control valve 31, and is preferably sized for transmitting a pressurized fluid from balloon inflation mechanism 34 (shown in FIG. 1) into the interior of balloon 32 through inflation openings 74 to inflate balloon 32.

Sensor cable lumen 62 (FIG. 3A) extends substantially parallel to lumen 54 along the length of handle 30 from first end 44 to second end 46. Lumen 62 is sized for receiving sensor cable 51. Sensor cable 51 extends through lumen 62 to temperature sensing device 36 at second end 46 of handle 30.

Insertion lumen 70 extends substantially parallel to lumens 54 and 62 (FIG. 3A) along the length of handle 30 from first end 44 to second end 46, and further extends through the interior of balloon 32 within balloon supporting member 73 to tip 78. Insertion lumen 70 preferably terminates at its distal end at ventilation opening 72 in tip 78, so that insertion lumen 70 is in fluid communication with the interior of the rectum when balloon 32 is inflated and positioned in the rectum. The interface between insertion lumen 70 and tip 78 is discussed in detail below with respect to FIG. 5. Insertion lumen 70 also receives introducer 80 (shown in detail in FIG. 4) to obturate insertion lumen 70 when balloon 32 is uninflated to facilitate insertion of balloon 32 into the rectum. The passageway formed through ventilation opening 72 and insertion lumen 70 is of a sufficient size to permit gas built up in the rectum to escape, acting as a ventilation duct to relieve pressure in the rectum during treatment.

Balloon 32 includes proximal waist 66 and distal waist 69, and is preferably integrally formed as part of a unitary structure of the same material. Balloon 32 has an outer diameter, when inflated, that radially increases from proximal balloon waist 66 to a point 68 generally midway between proximal balloon waist 66 and distal balloon waist 69, and that radially tapers from point 68 to distal balloon waist 69. Balloon 32 preferably has a nominal inflation volume of about 120 milliliters and a nominal diameter of about 4.8 centimeters (1.9 inches). Balloon 32 supports temperature sensing device 36 against the tissue of rectum 18 as shown in FIG. 1. Temperature sensing device 36 may be bonded to the inside or outside surface of balloon 32, or may be attached and contained in a groove formed in balloon 32 as described in further detail in U.S. Pat. No. 5,792,070 entitled RECTAL THERMOSENSING UNIT, by J. Kauphusman, J. Flachman and B. Neilson, which is hereby incorporated by reference. Distal waist 69 is located at a second end 50 of balloon 32 to allow fusing to balloon supporting member, as described below with respect to FIG. 5.

FIG. 3A is a cross-sectional view taken along lines 3A—3A of FIG. 2 illustrating handle 30 in greater detail. Balloon inflation lumen 54, sensor cable lumen 62 and insertion lumen 70 are preferably arranged in a generally triangular fashion and are isolated from one another as they extend through central body 40 of handle 30. In an alternative embodiment, sensor cable lumen 62 and insertion lumen 70 may be arranged within a central tube and balloon inflation lumen 62 may be realized as a coaxial chamber surrounding the central tube. Many other configurations of the lumens are also possible. FIG. 3B is a cross-sectional view taken along lines 3B—3B of FIG. 2 illustrating balloon supporting member 73 in greater detail. Balloon inflation lumen 54 and insertion lumen 70 are isolated from one another as they extend through balloon supporting member 73.

FIG. 4 is a side elevational view of introducer 80 for inserting into insertion lumen 70 in handle 30 and balloon supporting member 73 to facilitate insertion of balloon 32 into the rectum. Introducer 80 has first end 81 and second end 85. Introducer 80 has a wide shaft portion 82 adjacent first end 81, and has a long, narrow shaft portion 84 extending from end 83 of wide shaft portion 82 opposite first end 81 to second end 85. Introducer 80 is sized to be insertable into insertion lumen 70 of rectal probe 16. Together with balloon supporting member 73, introducer 80 (when inserted in insertion lumen 70) provides sufficient column strength to allow probe 16 to be inserted into the rectum of a patient without the need for digital manipulation or a separate external insertion tool to be manipulated by a doctor. Employing introducer 80 to provide the additional column strength allows balloon supporting member 73 to be formed of a relatively flexible material, such as urethane or silicone, so that balloon supporting member 73 (with introducer 80 removed) is not so rigid as to cause undesirable deformation of the rectal wall toward the prostate when balloon 32 is inflated. Introducer 80 is preferably formed of a rigid plastic or a wound or braided metal material to provide the required column strength, while still permitting some degree of flexibility during insertion to avoid trauma to the rectum. The proper depth of insertion is insured by positioning the radial shoulder at end 83 of wide shaft portion 82 of introducer 80 against first end 44 of handle 30. Wide shaft portion 82 of introducer 80 is therefore formed with a greater outer diameter than the inner diameter of insertion lumen 70 and than the outer diameter of narrow shaft portion 84. In operation, introducer 80 is inserted into insertion lumen 70, a doctor grasps handle 30 and inserts rectal thermosensing probe 16 into the rectum of a patient, introducer 80 is removed from insertion lumen 80, and balloon 32 is inflated within the rectum. The use of introducer 80 effectively stiffens balloon supporting member 73, therefore expediting the insertion process and reducing the degree of skill and care required on the part of the physician to insert rectal thermosensing probe 16. Alternatively, another manner of stiffening balloon supporting member 73 may be employed, such as by circulating pressurized fluid through insertion lumen 70 and closing ventilation opening 72, for example. It will be apparent to one skilled in the art that several methods of stiffening balloon supporting member 73 may be considered.

Figure 5:
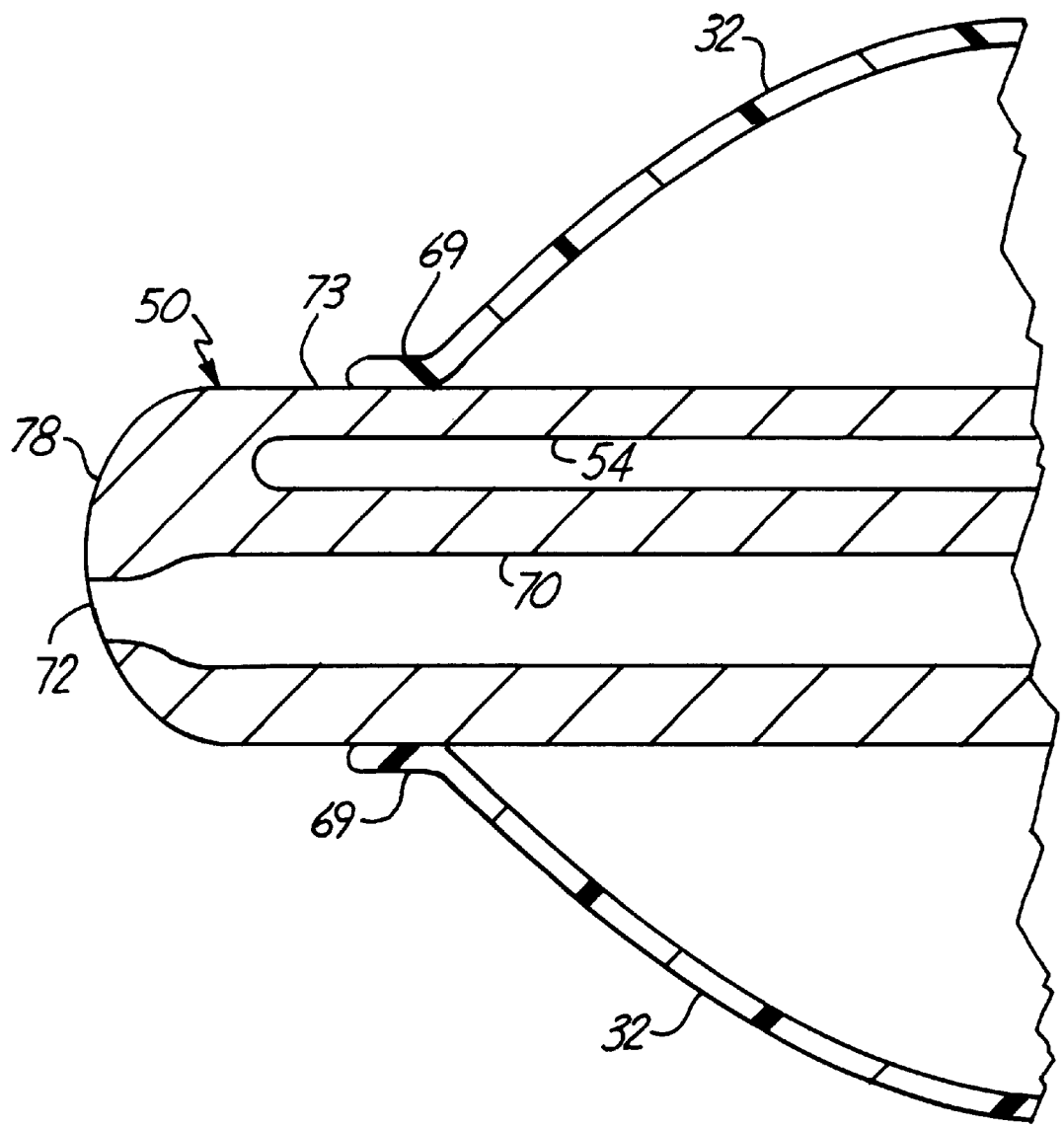
FIG. 5 is an enlarged side elevational view of a proximal end of the rectal thermosensing unit of FIG. 2 with portions shown in section.

FIG. 5 is an enlarged side elevational view of second end 50 of rectal thermosensing probe 16, with portions shown in section. Balloon 32 is fused to balloon support member 73 in a manner known in the art. Tip 78 is preferably fashioned by thermoforming the distal end of balloon support member 73 in a rounded shape, such that tip 78 is simply a shaped distal portion of balloon support member 73. Insertion lumen 70 and sensor cable lumen 54 are defined by the interior material forming balloon support member 73. Alternatively, tip 78 may be a separate silicone or thermoplastic piece for attachment to balloon support member 73, or may be a molded portion of balloon 32 for attachment to balloon support member 73. Ventilation opening 72 extends through tip 78 in fluid communication with insertion lumen 70. When inserted into insertion lumen 70, introducer 80 (FIG. 4) preferably does not extend into ventilation opening 72, assuring that introducer 80 does not project beyond tip 78.

The rectal thermosensing probe of the first embodiment of the present invention as described above therefore provides an improved rectal thermosensing probe for sensing the temperature of rectal tissue of a patient. The probe is a balloon thermosensing probe that supports a temperature sensing element against a wall of the rectum adjacent the prostate to provide accurate temperature readings. The probe includes a insertion lumen for allowing gas to escape from the rectum when the balloon is inflated, and for receiving a introducer to provide additional column stiffness and thereby facilitate insertion of the probe when the balloon is uninflated.

B. Foam Body Rectal Thermosensing Probe

FIG. 6 is a side view of rectal thermosensing device 110 according to a second embodiment of the present invention. Rectal thermosensing device 110 includes passively expandable body 112, temperature sensing strip 114, ventilation tube 116, orientation flag 118 and handle 120. Body 112 is preferably composed of an approximately two pound density open-cell foam such as a molded polyurethane or polyester, for example, but may alternatively be composed of closed-cell foam as well. In an uncompressed state, body 112 has an outer diameter which approximates a diameter of a rectal cavity. Body 112 has a relatively low durometer characteristic, so that body 112 is able to conform to the shape of the rectal cavity without displacing the rectal wall toward the prostate or compressing rectal tissue. Body 112 may have a non-permeable coating on it, or may alternatively be composed of a self-skinning foam. The non-permeable coating may be a urethane adhesive epoxy, as is known in the art.

Body 112 has a first end 119, which is inserted into the rectal cavity, and a second end 121 which lies outside the rectal cavity. Body 112 is preferably supported by a longitudinal member between first end 119 and second end 121 such as ventilation tube 116, there by permitting self-expansion of body 112 to conform to the shape of a rectal cavity. In one embodiment, body 112 has a substantially linear longitudinal axis. Body 112 may be formed by injection molding or by contouring its outer surface with a lathe, for example, or by any of several alternative techniques known in the art.

Temperature sensing strip 114 is attached to the outer surface of body 112, extending from handle 120 toward first end 119 of body 112. Temperature sensing strip 114 may, for example, be a flattened tube that receives a circuit strip for mounting a plurality of thermosensing elements, such as thermal sensors or resistive temperature devices (RTDs), for example. An exemplary temperature sensing strip design is shown in the aforementioned U.S. Pat. No. 5,792,070, entitled RECTAL THERMOSENSING UNIT by J. Kauphusman, J. Flachman and B. Neilson, which has been incorporated herein by reference.

The rectal thermosensing device 110 of the second embodiment of the present invention is employed during a transurethral microwave thermal therapy treatment, which typically lasts for approximately one hour. To ensure comfort during the treatment for the patient, thermosensing device 110 is provided with ventilation tube 116, which extends along the length of rectal thermosensing device 110 through handle 120 and body 112, terminating at opening 117 at the first end 119 of body 112. Ventilation tube 116 is of a sufficient size to permit gas built up in the rectum to escape while rectal thermosensing device 110 is located in the rectal cavity. Ventilation tube 116 also provides increased column strength to the rectal probe for ease of insertion. In preferred embodiments, ventilation tube 116 may be formed of vinyl, plastic or rubber tubing, for example, or alternatively may itself be composed of foam, with a sheath deployed around body 112 to provide the necessary column strength for insertion. Ventilation tube 116 is bonded within a preformed passageway within body 112. In one preferred embodiment, this preformed passageway may be formed by a hot wire press, for example, or by an alternative technique known in the art. Alternatively, a ventilation path may be provided by forming a groove or recess in the outer diameter of body 112, opposite temperature sensor 114 for example, to prevent complete sealing of the rectum upon insertion of rectal thermosensing unit 110.

Flag 118 generally comprises an elongate protrusion integrally connected to handle 120 and radially extending outward from handle 120 at a selected angle or position relative to body 112 and temperature sensing strip 114. Flag 118 indicates the orientation of body 112 and temperature sensing strip 114 within the rectum during treatment. Flag 118 further indicates when body 112 and temperature sensing strip 114 have been fully inserted into the rectum. As can be appreciated, a variety of indicating mechanisms such as indexing marks, grooves or alternative projections may be used in lieu of flag 118 for permitting a physician to visually determine the orientation and location of body 112 and temperature sensing strip 114 within the rectum.

FIG. 7 is a sectional view taken along line 7—7 in FIG. 6, and FIG. 8 is a sectional view taken along line 8—8 in FIG. 6. FIG. 7 illustrates temperature sensing strip 114 mounted on an outside surface of body 112, with ventilation tube 116 extending through foam body 112. FIG. 8 illustrates handle 120 having flag 118 protruding therefrom, with ventilation tube 116 extending through handle 120 and temperature sensing strip 114 being mounted to the outside of handle 120, and extending along an outside surface of body 112.

Figure 9:
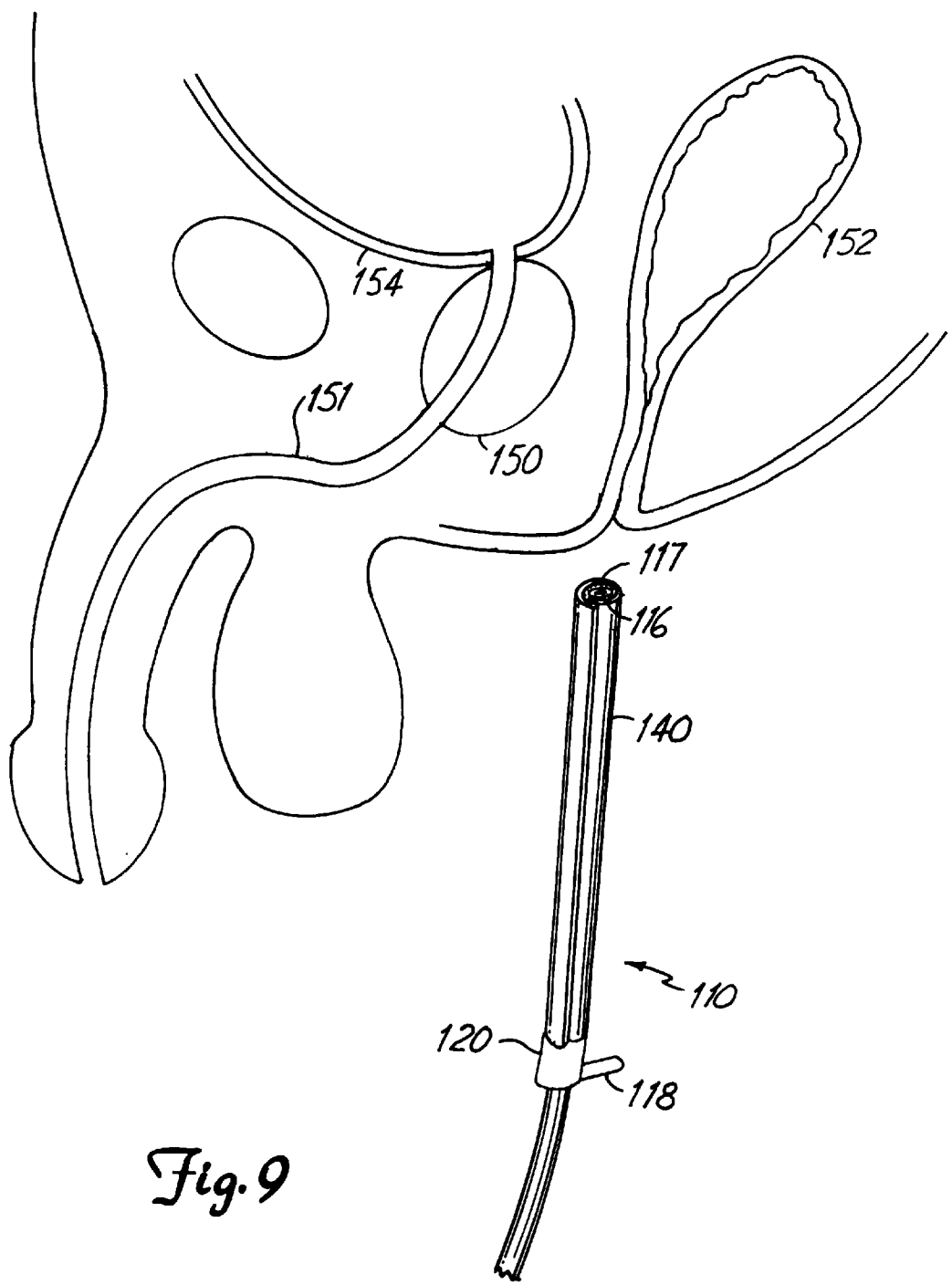
FIG. 9 is a diagram illustrating the rectal thermosensing unit of the second embodiment of the present invention compressed in preparation for insertion into a rectum.
Figure 10:
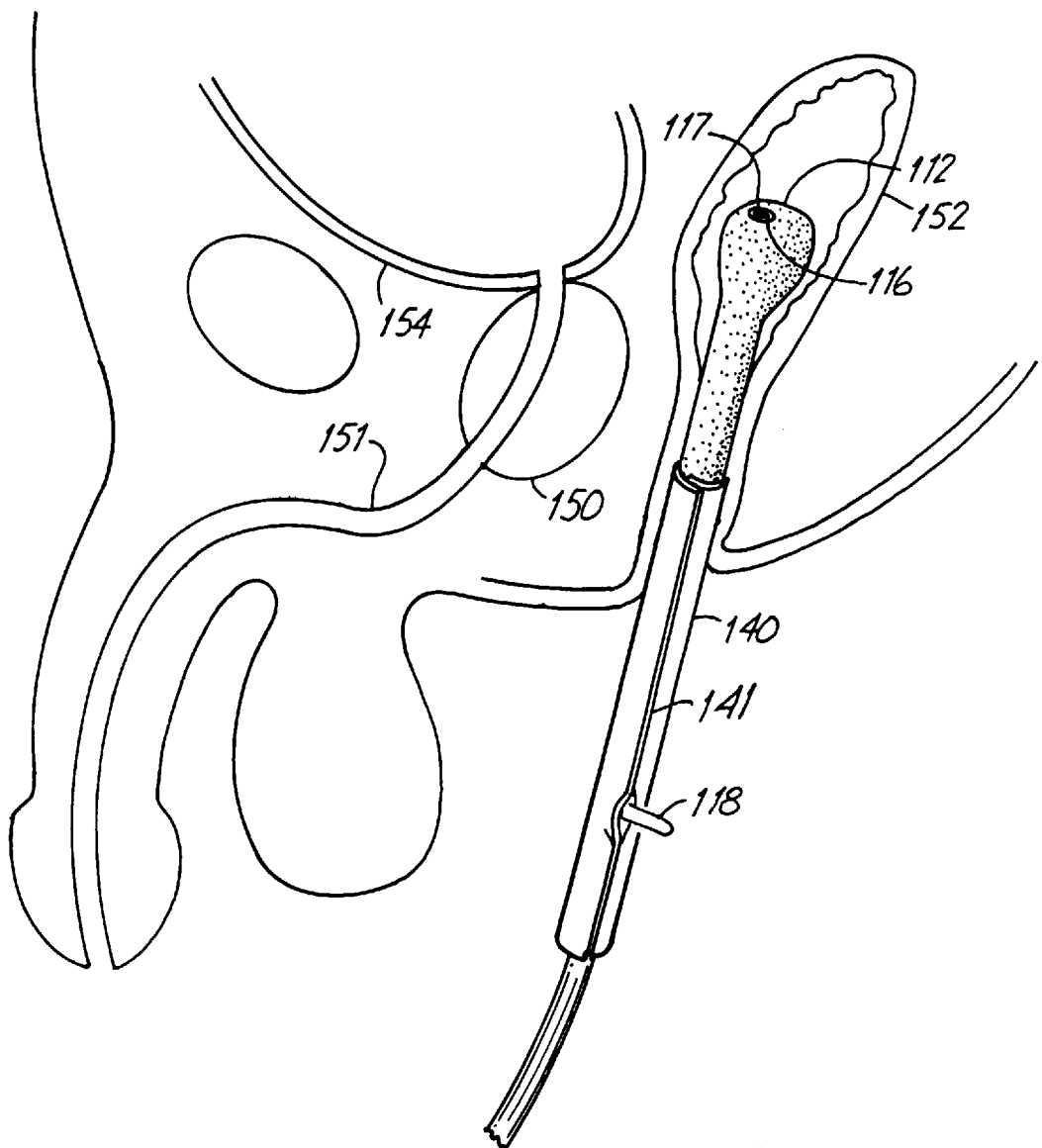
FIG. 10 is a diagram illustrating the rectal thermosensing unit of the second embodiment of the present invention in situ immediately after insertion into the rectum.
Figure 11:
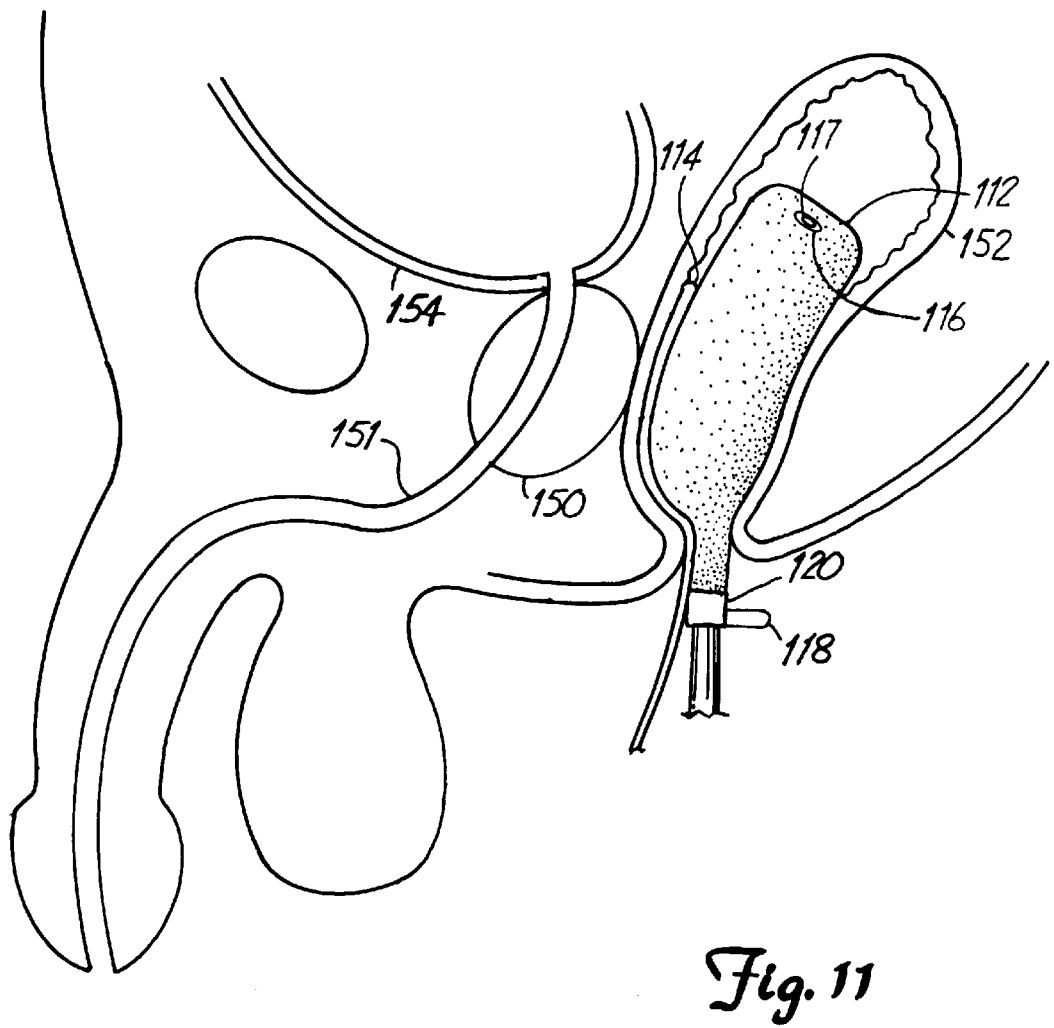
FIG. 11 is a diagram illustrating the rectal thermosensing device of second embodiment of the present invention in situ after it has expanded to conform to the walls of the rectum.

FIGS. 9–11 depict the use and operation of rectal thermosensing unit 110. As generally shown in FIG. 9, the male pelvic region includes prostate 150, urethra 151, rectum 152 and bladder 154. In transurethral thermal therapy, a microwave antenna-containing catheter (not shown) is inserted into urethra 151 at the level of prostate 150, to deliver microwave energy sufficient to heat and necrose diseased tissue in prostate 150. As shown in FIG. 9, sheath 140 is initially placed around body 112 of rectal thermosensing unit 110, thereby compressing body 112 to a diameter small enough for insertion through the anus into rectum 152. A preferred diameter of sheath 140 is about 0.5–0.7 inches, for example.

FIG. 10 is a diagram illustrating rectal thermosensing unit 110 in situ immediately after insertion into rectum 152. Sheath 140 containing body 112 has been inserted into rectum 152, and sheath 140 has been partially withdrawn, so that body 112 has begun to passively expand within rectum 152. Sheath 140 includes slit 141 so that withdrawal of sheath 140 is not impeded by orientation flag 118 on handle 120 of rectal thermosensing device 110.

FIG. 11 is a diagram illustrating rectal thermosensing device 110 in situ after it has passively expanded to conform to the walls of rectum 152. After sheath 140 is completely removed from body 12, the passively expandable material naturally expands to conform to the shape of rectum 152, thereby positioning temperature sensing strip 114 in contact with the wall of rectum 152 adjacent prostate 150. Ventilation tube 116 extends through body 112, permitting gas built up in rectum 152 to escape and thereby relieving pressure in rectum 152 during treatment. Body 112 of rectal thermosensing unit 110 passively expands with a low amount of force, as dictated by the density of the foam or other material composing body 112, such as the preferred approximately two pound density open-cell foam, so that the wall tissue of rectum 152 is not compressed, thereby ensuring proper blood flow through the veins in the rectal wall. Orientation flag 118 on handle 120 indicates the orientation of body 112 and temperature sensing strip 114 when they are inserted in rectum 152. After the therapy has been completed, body 112 may be removed by simply pulling handle 120, since body 112 is readily compressible and will therefore compress to the diameter of the anus as the unit is removed.

FIG. 12 is a side view of an alternate version of rectal thermosensing device 110 for insertion into a rectum. The curved shape depicted in FIG. 12 generally conforms to the natural curvature of the rectal cavity, having a substantially arcuate longitudinal axis, thereby providing a conforming fit and position of body 112 within the rectal cavity without displacing or compressing rectal wall tissue. For insertion purposes, sheath 140 (FIGS. 9–11) also is curved with the same general contour as body 112.

FIG. 13 is an exploded perspective view of rectal thermosensing device 110 according to another alternate version of the second embodiment of the present invention. In the alternate version shown in FIG. 13, rectal thermosensing unit 110 is provided with a recessed groove 130 formed in body 112. Groove 130 receives temperature sensing strip 114 so that temperature sensing strip 114 lies flush with the outer surface of body 112. Temperature sensing strip 114 is preferably secured in groove 130 in body 112 by thermal bonding, for example, or another alternative adhesive bonding technique.

FIG. 14 is a sectional view taken along line 14—14 in FIG. 13, illustrating the cross-section of body 112. Temperature sensing strip 114 is received in groove 130 to present a substantially circular uniform cross-section of body 112. Ventilation tube 116 extends through body 112 in the same manner as in the embodiment shown in FIG. 6.

The rectal thermosensing device of the second embodiment of the present invention therefore supports a temperature sensing element against a rectal wall adjacent the prostate during transurethral thermal therapy to provide a physician with a temperature of rectal tissue for controlling the heat delivered during the thermal therapy treatment. Rectal tissue is not compressed by the passively expandable body of the rectal thermosensing device. The device minimizes the risk of human error, since the body cannot be over-inflated like prior art balloon devices. Temperature sensing devices on the rectal thermosensing device may be reused by simply removing the temperature sensing device from one body probe and attaching it to another body probe. The passively expandable body of the rectal thermosensing device of the present invention is also typically less expensive to produce than previous balloon probes.

Although the present invention has been described with reference to preferred embodiments, workers skilled in the art will recognize that changes may be made in form and detail without departing from the spirit and scope of the invention.

What is claimed is:

1. A rectal thermosensing unit comprising:
   an elongate member;
   an inflation lumen extending through the elongate member;
   an inflatable balloon supported by the elongate member, an interior of the inflatable balloon being in fluid communication with the inflation lumen;
   an insertion lumen extending through the elongate member;
   an introducer insertable into the insertion lumen; and
   a temperature sensing device supported by the inflatable balloon.

2. The rectal thermosensing unit of claim 1, wherein the inflatable balloon has a first end attached to the elongate member and a second end forming a tip.

3. The rectal thermosensing unit of claim 2, wherein the insertion lumen extends through the elongate member and the tip to form a ventilation opening in the tip.

4. The rectal thermosensing unit of claim 1, wherein the introducer includes a wide shaft portion and a narrow shaft portion, the narrow shaft portion being receivable by the insertion lumen and the wide shaft portion having an outer diameter greater than an inner diameter of the insertion lumen.

5. A method of locating in a rectum a rectal thermosensing probe having an elongate member supporting an inflatable balloon in a rectum, the inflatable balloon supporting a temperature sensing device, the method comprising:
   providing an inflation lumen and an insertion lumen extending through the elongate member;
   inserting an introducer into the inflation lumen;
   inserting the inflatable balloon supported by the elongate member having the introducer inserted in the insertion lumen therein into the rectum;
   removing the introducer from the insertion lumen; and
   inflating the inflatable balloon by providing fluid through the inflation lumen.

6. The method of claim 5, wherein the introducer includes a wide shaft portion and a narrow shaft portion, the narrow shaft portion being receivable by the insertion lumen and the wide shaft portion having an outer diameter greater than an inner diameter of the insertion lumen, and wherein the step of inserting the introducer into the insertion lumen comprises inserting the narrow shaft portion of the introducer into the insertion lumen.

7. A rectal thermosensing unit comprising:
   a passively expandable body having a first end and a second end;
   an elongate member supporting the passively expandable body between the first and second ends;
   a temperature sensing device supported by the passively expandable body;
   a handle at the second end of the passively expandable body; and
   a ventilation tube extending through the handle and through the passively expandable body between the second end and the opening in the first end.

8. The rectal thermosensing unit of claim 7, wherein the passively expandable body is composed of an open-cell foam.

9. The rectal thermosensing unit of claim 7, further comprising:
   a sheath deployable around the passively expandable body to compress the passively expandable body to a preselected diameter for insertion into a rectum.

10. A method of sensing temperature of rectal tissue, comprising:
    compressing a passively expandable body having an uncompressed outer diameter approximating a rectal cavity, the passively expandable body carrying at least one temperature sensor;
    inserting the compressed passively expandable body into the rectal cavity; and
    allowing the passively expandable body to expand to conform to a shape of the rectal cavity.

11. The method of claim 10, wherein the passively expandable body has first and second ends and is supported by an elongate member between the first and second ends.

12. The method of claim 11, wherein the passively expandable body includes an opening at the first end and the elongate member comprises a ventilation tube extending from the second end to the opening in the first end.

13. The method of claim 10, wherein the step of compressing the passively expandable body comprises deploying a sheath around the passively expandable body, and wherein the step of allowing the passively expandable body to expand to conform to the shape of the rectal cavity comprises removing the sheath from the passively expandable body.

14. A method of forming a rectal thermosensing unit, comprising:
    forming a passively expandable body having an uncompressed outer diameter approximating a rectal cavity;
    forming a passageway through the passively expandable body;
    bonding an elongate member to the passively expandable body in the passageway;
    attaching a temperature sensing device to the passively expandable body; and
    attaching a handle to the elongate member.

15. The method of claim 14, wherein the passively expandable body has first and second ends and includes an opening in the first end, and wherein the elongate member comprises a ventilation tube extending through the handle and through the passively expandable body between the second end and the opening in the first end.

16. The method of claim 14, wherein the passively expandable body is composed of an open-cell foam.

17. The method of claim 14, further comprising:
    forming a sheath deployable around the passively expandable body to compress the passively expandable body to a preselected diameter for insertion into a rectal cavity.

* * * * *